United States Patent [19]

Yee

[11] 4,278,561

[45] Jul. 14, 1981

[54] FLUORINATED BENZENESULFONATE DIACETYLENES

[75] Inventor: Kwok C. Yee, Randolph, N.J.

[73] Assignee: Allied Chemical Corporation, Morris Township, Morris County, N.J.

[21] Appl. No.: 942,089

[22] Filed: Sep. 13, 1978

[51] Int. Cl.$^3$ ............................................... C09K 3/00
[52] U.S. Cl. ............................... 252/408; 204/159.11; 422/56; 73/356; 116/207; 250/474; 260/456 P; 426/87; 426/88; 526/285
[58] Field of Search ................... 526/285; 204/159.11; 23/253 TP; 73/356; 116/207; 426/87, 88; 252/408; 260/456 P; 250/474

[56] References Cited

U.S. PATENT DOCUMENTS

| | | | |
|---|---|---|---|
| 3,966,414 | 6/1976 | Khattab et al. | 116/207 |
| 3,999,946 | 12/1976 | Patel et al. | 23/253 TP |
| 4,154,107 | 5/1979 | Giezen et al. | 116/207 |

OTHER PUBLICATIONS

*Die Makromolekulare Chemie*, vol. 145, (1971) pp. 85-94 by Gerhard Wegner.
Acta Crystal (1978) B-34, pp. 143-147 and 147-151, by J. J. Mayerle and T. C. Clark.

*Primary Examiner*—Benjamin R. Padgett
*Assistant Examiner*—J. L. Barr
*Attorney, Agent, or Firm*—Robert A. Doernberg; Alan M. Doernberg; Gerhard H. Fuchs

[57] ABSTRACT

New fluorinated benzenesulfonate diacetylene compositions are described which are useful in time-temperature devices for monitoring the shelf-lives of perishable articles. The compositions are solid-state polymerizable by thermal annealing or exposure to actinic or high energy ionizing radiation. Some of the compositions, in addition, exhibit relatively longer polymerization induction periods, compared to other known diacetylene compositions, and an "autocatalytic" effect upon polymerization during which a rapid color change occurs. These characteristics are extremely useful in monitoring situations which require a striking color change as an indication that a particular time-temperature history profile, e.g. shelf-life, has expired.

12 Claims, 3 Drawing Figures

FLUORINATED BENZENESULFONATE DIACETYLENES

BACKGROUND OF THE INVENTION

1. Field of the Invention

This invention relates to new fluorinated benzenesulfonate diacetylene compositions useful in time-temperature history monitoring devices.

2. Brief Description of the Prior Art

Diacetylene compositions, containing at least one conjugated diyne grouping, i.e., —C≡C—C≡C—, and including benzenesulfonate derivatives, are known to be useful in time-temperature history monitoring devices as exemplified in U.S. Pat. No. 3,999,946 (Patel et al. to Allied Chemical, 1976), which is hereby incorporated by reference. As described in the reference, the unique crystal packing and chain alignment of solid monomeric diacetylene compositions, enables them to be polymerized in the solid state by actinic or high energy ionizing radiation, or thermal annealing, thereby producing a colored polymer having a fully conjugated polymer backbone. Generally, the hue and intensity of the resulting observed color is a function of the degree of polymerization, which in turn is a function of the integrated time-temperature history or radiation-dosage history to which the composition has been subjected.

A general characteristic of the solid monomeric diacetylene compositions is that, upon thermally induced solid state polymerization, a gradual increase in the hue and intensity of produced color normally occurs. Advantage can be taken of this characteristic in time-temperature history devices, which are not "on-off" or "go-no-go" type devices, for example, by pretreating the compositions for different time periods and then forming an array in which a gradual change occurs along the array, thus producing a visual moving boundary. Devices of this type are described in U.S. Application Ser. No. 839,542 (filed Oct. 5, 1977, R. Baughman et. al to Allied Chemical). However, these devices normally require an attached color reference chart for ascertaining the extent of the accumulated time-temperature history of the compositions or a highly refined pretreatment procedure meeting rigid quality control standards which can be expensive and add to the total cost of producing such devices.

What is desired in an "on-off" or "go-no-go" device is a composition which does not exhibit a gradual increase in developed hue and intensity, but one that remains colorless, or nearly so, until the desired known time-temperature history interval or shelf-life of an article being monitored has been reached, whereupon a striking color change occurs just prior to the expiration of said interval. Such a composition should undergo a small degree of polymerization before a certain time-temperature history interval is reached, termed a "long polymerization induction period," and when the desired interval is reached, the composition should exhibit an accelerated rate of polymerization, termed as "autocatalytic polymerization effect". The mechanisms underlying the polymerization inductive period and autocatalytic effect are not clearly understood.

Only one diacetylene composition in the prior art is known to exhibit this behavior, the bis(p-toluene sulfonate) of 2,4-hexadiyn-1,6-diol, referred to herein as PTS, whose properties upon thermal polymerization are described in the article *Die Makromolekulare Chemie* Vol. 145 (1971) pp 85–95 by Gerhard Wegner. From this teaching it could be inferred that para-substituted benzene sulfonates of diacetylenic diols, in general, might exhibit relatively long polymerization induction periods coupled with autocatalytic polymerization effects in the region of a desired integrated time-temperature history of an article.

However, the reference *Acta Cryst.* (1978) B-34, pp. 143–147 by J. J. Mayerle and T. C. Clark, discloses that the bis(p-chlorobenzenesulfonate) of 2,4-hexadiyn-1,6-diol does not undergo solid state polymerization upon thermal annealing or exposure to X-ray irradiation. The authors indicate that the particular packing characteristics of the crystals, which are dominated by non-bonded Cl-Cl and Cl-C (phenyl) interactions, which in turn interfere with monomer packings, are responsible for interfering in the solid-state polymerization process of the solid compound.

We have independently shown that bis(p-bromobenzenesulfonate), bis(p-nitrobenzenesulfonate), bis(p-methoxybenzenesulfonate) and bis(2,4,5-trichlorobenzenesulfonate), of 2,4-hexadiyn-1,6-diol, are all inactive to solid state polymerization upon thermal annealing.

Thus, the implied assumption in the prior art, that all halogenated benzenesulfonates of diacetylenic diols are capable of undergoing solid state polymerization is misleading.

What is needed and what the prior art does not describe the halogenated benzenesulfonate derivatives of acetylenic diols, preferably a definable class of such diacetylenes, capable of undergoing solid state polymerization and preferably exhibiting relatively long polymerization induction periods coupled with autocatalytic polymerization effects.

SUMMARY OF THE INVENTION

We have unexpectedly found that fluorinated benzenesulfonate diacetylene compositions, as a definable class, are all capable of undergoing solid state polymerization, and in some cases exhibit long polymerization induction periods coupled with autocatalytic behavior during solid state polymerization.

By the term "long polymerization induction period" as used herein, is meant that upon exposure to thermal annealing, very little color change occurs, e.g. color development upon thermal annealing, during about the first 10% of polymerization, as contrasted to other diacetylenes, for example, diacetylene diol urethanes. Among the urethane derivatives, for example, 2,4-hexadiyn-1,6-diol bis(phenylurethane), a color change occurs almost immediately and results in a gradual color change up to the end point color. The longer induction period of some of the fluorinated benzenesulfonate derivatives of this invention allows a greater time frame for the monitoring of time-temperature histories of perishable articles.

By the term "autocatalytic effect," as used herein, is meant that a dramatic increase in the rate of polymerization occurs immediately after the polymerization induction period without any addition of catalyst.

The advantages of these compositions listed below include the fact that, as a definable class, they can be used in devices for monitoring the time-temperature histories and shelf-lives of perishable articles as opposed to other known halogenated benzene sulfonate diacetylene compositions. Two members of the class, the bis(p-fluorobenzenesulfonate) and bis(m-trifluoromethylbenzensulfonate) of 2,4-hexadiyn-1,6-diol, exhibit very little color change upon thermal annealing, i.e., exposure to the particular temperature being monitored, up to about 10 percent polymerization, thus exhibiting relatively long polymerization induction periods. Continued annealing above this point leads to a rapid increase in the rate of polymerization and consequently an abrupt dramatic, constrasting color change, as for example, from a light pink to a dark red or metallic-gold color, said contrasting color change, being one that is very evident to the average observer. By choosing one of the compositions which exhibits this autocatalytic effect just prior to the expiration of the shelf-life of a perishable, adequate warning to the customer, retailer, manufacturer, or wholesaler will be given to indicate that the perishable is no longer suitable for use or sale. This type of warning is especially critical and needed in the case of pharmaceuticals.

A further advantage of the subject compositions is that at least one member thereof possesses a higher energy of activation, $E_{act}$, than PTS, described above by Wegner. For example, bis(p-fluorobenzenesulfonate) of 2,4-hexadiyn-1,6-diol has a measured energy of activation of about 26 kcal/mole, whereas that of PTS is about 22 kcal/mole. This increase allows the bis(p-fluorobenzenesulfonate) composition to be used in monitoring shelf-lives of perishables over longer and higher temperature profiles than is possible with PTS. Usual activation energies of diacetylene compounds described in the prior art are in the order of about 20–22 kcal/mole.

Partially polymerized fluorinated benzenesulfonated diacetylene compositions containing up to 10 weight percent polymer, and polymerized benzenesulfonate diacetylene compositions, containing from 10 to 100% by weight) are both novel classes of compositions which are also subjects of this invention. They are useful as reference standards in the above-described device and can also be employed in preparing films and fibers having semiconductive, photoconductive and optical properties.

In accordance with this invention, there is provided a composition of the following formula:

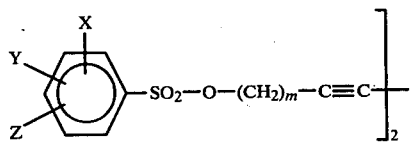

wherein m is an integer value from 1 to 4 and X, Y and Z are selected from hydrogen, fluoro and $C_1$–$C_4$ fluorinated normal, iso- or secondary alkyl, containing 1–9 fluorine atoms, said composition being symmetrical and containing at least two fluorine atoms and being capable of undergoing solid state polymerization upon thermal annealing or exposure to actinic radiation or high energy ionizing radiation.

It is to be understood that the symbols X, Y and Z represent radicals on the benzene ring as described herein, but in no particular assigned ring position and, with the proviso that whatever the actual positions of the radicals are, the resulting molecular geometry is symmetrical.

Also there is provided a colored composition containing up to 10% by weight of a colored polymer derived from at least one monomer composition as defined above.

Further, there is provided a composition containing from 10 to 100% by weight of a colored polymer derived from at least one monomer composition as defined above.

In addition, there is provided in a device for monitoring the time-temperature history of a perishable including a housing, in which is positioned a time-temperature indicating material, capable of undergoing solid state polymerization upon thermal annealing to produce a contrasting color change, prior to the expiration of the shelf life of said article and means for observing said color change; the improvement which comprises providing a monomer composition described above as the time-temperature indicating material.

DESCRIPTION OF THE INVENTION AND PREFERRED EMBODIMENTS

Figure 1:
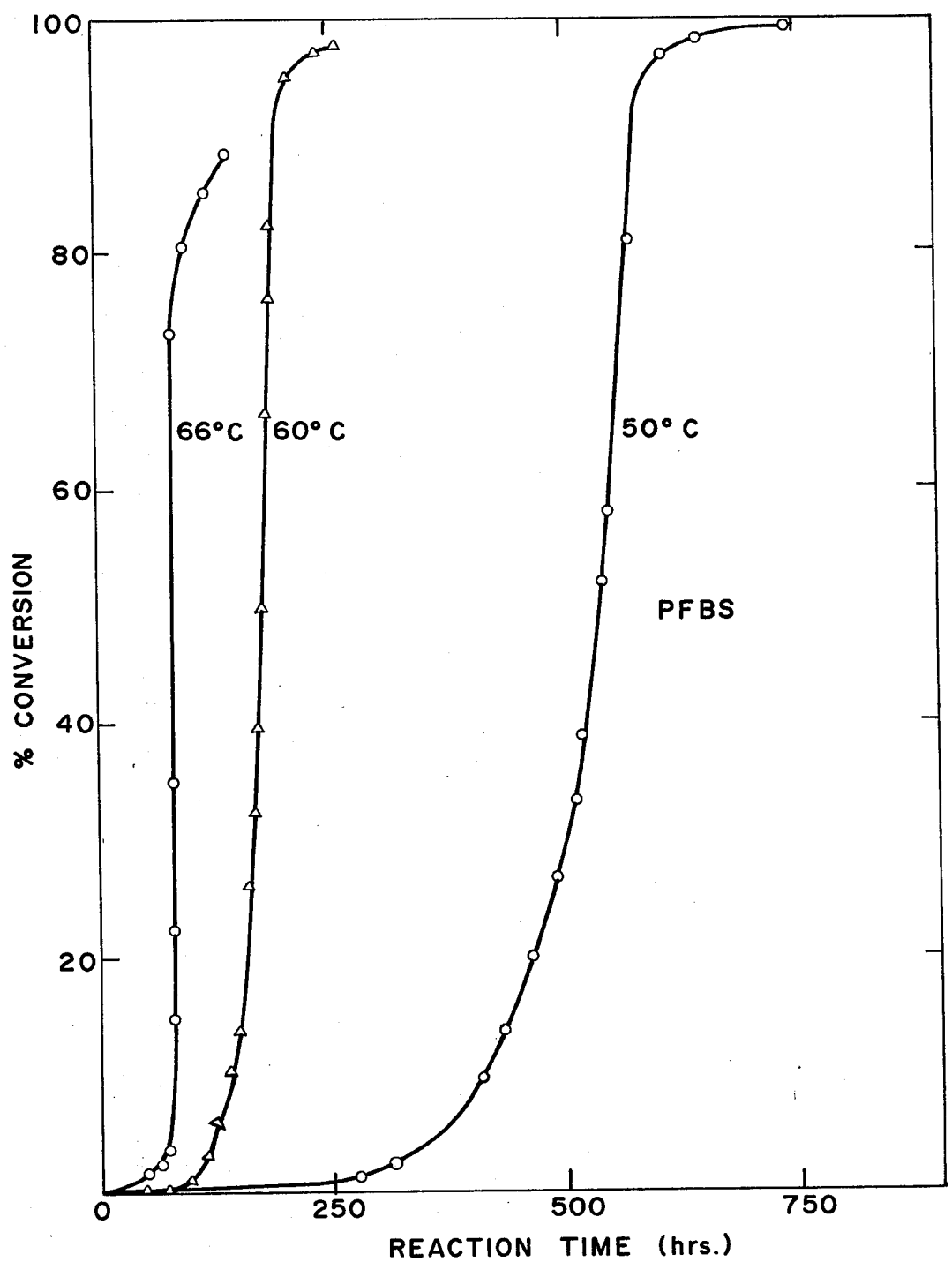
FIG. 1 illustrates the effect of thermal annealing on bis(p-fluorobenzenesulfonate) of 2,4-hexadiyn-1,6-diol (PFBS) by a plot of percent conversion to polymer vs. reaction time in hours at a given temperature.

The subject compositions of this invention are fluorinated benzenesulfonate diacetylene compounds of the above-described formula which contain at least two fluorine atoms, are symmetrical, and are capable of undergoing solid state polymerization by thermal annealing or exposure to actinic radiation or high energy ionizing radiation. By the term "solid state polymerization" as used herein, is meant the process of the monomer undergoing 1,4-addition polymerization by virtue of the close packing of the monomers in the crystalline solid. The term "solid" also is construed to cover partially amorphous solids as well, as long as they are capable of undergoing polymerization upon thermal annealing by the methods described herein. By the term "thermal annealing," as used herein, is meant exposure to a temperature below the melting point of the composition sufficient to induce polymerization to occur. By the term "actinic radiation" as used herein, is meant visible or ultraviolet radiation. By the term "high energy ionizing radiation" as used herein, is meant gamma radiation, laser beam, electron beam, X-rays, beta rays and the like. By the term "$C_1$–$C_4$ fluorinated . . . alkyl," as used herein, is meant an alkyl group containing 1–4 carbon atoms and containing from 1–9 fluorine atoms.

A preferred subclass of the above subject compositions is where X and Y, in the above-described formula, are hydrogen. A preferred subclass within this subclass is where Z is selected from m-fluoro, p-fluoro, m-trifluoromethyl and p-trifluoromethyl.

The fluorinated benzenesulfonate diacetylene compositions of this invention can be prepared by reacting a substituted benzenesulfonyl halide with an acetylenic diol according to the general method described in Makromol. Chem. 145, 85–94 (1971), hereby incorporated by reference, and described in Examples 1-6 herein. In general, the fluorinated benzenesulfonyl halides and acetylenic diols are dissolved in a suitable solvent therefor and the resulting solution chilled to about 0° to 10° C. A molar ratio of about 2.5:1 of the sulfonyl halide to the diol is used. Potassium hydroxide, either in the solid powdered form or as an aqueous solution, is then added slowly to the well stirred solution. After the addition, the contents are allowed to stir. The product is then isolated from the resulting mixture and purified by conventional methods such as recrystallization from a suitable solvent.

Choice of recrystallization solvent in some instances has an effect on the properties of the final fluorinated benzenesulfonate composition. For example, bis(p-fluorobenzenesulfonate) of 2,4-hexadiyn-1,6-diol exhibits a longer polymerization induction period and sharper autocatalytic effect, when recrystallized from acetone-petroleum ether, as compared to recrystallization from acetone. It will be obvious to one skilled in the art as to how to improve the color-indicating properties of the subject compositions by the disclosure herein.

Representative fluorinated benzenesulfonyl halides, useful in preparing the subject compositions, are given below in Table I.

TABLE I p-fluorobenzenesulfonyl chloride
p-fluorobenzenesulfonyl bromide
p-fluorobenzenesulfonyl fluoride
p-fluorobenzenesulfonyl iodide
m-fluorobenzenesulfonyl iodide
o-fluorobenzenesulfonyl iodide
m-fluorobenzenesulfonyl bromide
m-fluorobenzenesulfonyl iodide
o-trifluoromethylbenzenesulfonyl iodide
2,4-difluoromethylbenzenesulfonyl chloride
p-trifluoromethylbenzenesulfonyl chloride
m-trifluoromethylbenzenesulfonyl chloride
2,4-di-(trifluoromethyl)benzenesulfonyl chloride
2,4,5-tri-(trifluoromethyl)benzenesulfonyl chloride
1,3,5-tri-(trifluoromethyl)benzenesulfonyl chloride
p-pentafluoroethylbenzenesulfonyl chloride
p-(2-fluoroethyl)benzenesulfonyl chloride
2-fluoro-4-trifluoromethylbenzenesulfonyl chloride
p-(nonafluoro-n-butyl)benzenesulfonyl chloride
p-(nonafluoro-isobutyl)benzenesulfonyl chloride
p-(nonafluoro-sec-butyl)benzenesulfonyl chloride Acetylenic diols useful in preparing the subject compositions are of the formula:

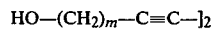

HO—(CH$_2$)$_m$—C≡C—]$_2$ wherein m is an integer value from 1 to 4. Listed below are the chemical names of the diols as a function of the value of m.

TABLE II

| Chemical Name | m |
| --- | --- |
| 2,4-hexadiyn-1,6-diol | 1 |
| 3,5-octadiyn-1,8-diol | 2 |
| 4,6-decadiyn-1,10-diol | 3 |
| 5,7-dodecadiyn-1,12-diol | 4 |

Representative examples of fluorinated benzenesulfonate diacetylenes of this invention prepared from the above fluorinated benzenesulfonyl halides and acetylenic diols include: the bis(p-fluorobenzenesulfonate), bis(m-fluorobenzenesulfonate, bis(o-fluorobenzenesulfonate), bis(2,4-difluorobenzenesulfonate), bis(p-trifluoromethylbenzenesulfonate), bis(m-trifluoromethylbenzenesulfonate), bis[2,4-di-(trifluoromethyl)benzenesulfonate], bis[2,4,5-tri(trifluoromethyl)benzenesulfonate], bis[1,3,5-tri-(trifluoromethyl)benzenesulfonate], bis(p-pentafluoromethylbenzenesulfonate), bis(p-2-fluoroethylbenzenesulfonate), bis(2-fluoro-4-trifluoromethylbenzenesulfonate), bis[p-(nonafluoro-n-butyl)benzenesulfonate], bis[p-(nonafluoroisobutyl)benzenesulfonate], and bis[p-(nonafluoro-secbutyl)benzenesulfonate] of 2,4-hexadiyn-1,6-diol; of 3,5-octadiyn-1,8-diol; of 4,6-decadiyn-1,10-diol and of 5,7-dodecadiyn-1,12-diol. Preferred compositions for use in time-temperature history indicators are bis(p-fluorobenzensulfonate) and bis(m-trifluoromethylbenzenesulfonate) of 2,4-hexadiyn-1,6-diol; bis(m-trifluoromethylbenzenesulfonate) of 4,6-decadiyn-1,10-diol and bis(p-fluorobenzenesulfonate) and bis(m-trifluoromethylbenzenesulfonate of 5,6-dodecadiyn-1,12-diol. Particularly preferred is the bis(p-fluorobenzenesulfonate) of 2,4-hexadiyn-1,6-diol.

Representative melting points of some fluorinated benzenesulfonate diacetylene compositions are listed below. These compositions exhibit solid state polymerization below their respective melting points.

TABLE III

| Composition | Melting Point (°C.) |
| --- | --- |
| bis(p-fluorobenzenesulfonate) of 2,4-hexadiyn-1,6-diol | 70 |
| bis(m-trifluoromethylbenzenesulfonate) of 2,4-hexadiyn-1,6-diol | 75 |
| bis(m-trifluoromethylbenzenesulfonate) of 4,6-decadiyn-1,10-diol | 68 |
| bis(m-trifluoromethylbenzene sulfonate) of 5,7-dodecadiyn-1,12-diol | 77 |
| bis(p-fluorobenzenesulfonate) of 5,7-dodecadiyn-1,12-diol | 69 |

The subject fluorinated benzenesulfonate diacetylene compositions are distinguished from other halogenated benzenesulfonate compositions in that they are solid state polymerizable. Usually, this property can be observed, in that a color change in the solid monomer occurs at room temperature under ambient sunlight conditions. Examples are given below for other halogenated benzenesulfonate derivatives, in addition to those described previously, which were found by the inventor not to be solid state polymerizable.

TABLE IV bis(p-bromobenzenesulfonate)
of 2,4-hexadiyn-1,6-diol
bis(p-chlorobenzenesulfonate)
of 2,4-hexadiyn-1,6-diol
bis(2,4,5-trichlorobenzenesulfonate)
of 2,4-hexadiyn-1,6-diol In addition to being solid state polymerizable, some members of the subject compositions exhibit the desirable dual characteristics of a relatively long polymerization induction period as well as an autocatalytic effect upon thermal annealing.

For example, the polymerization characteristics of bis(p-fluorobenzenesulfonate) of 2,4-hexadiyn-1,6-diol, referred to as PFBS, are illustrated in FIG. 1. It will be noted that the curve is "S"-shaped, by virtue of the fact that the compound exhibits an induction period in the initial stage of thermal annealing giving rise to a flat portion of the curve. After the induction period has elapsed, the autocatalytic effect begins to operate very rapidly, thus giving rise to the steep slope in the curve.

Figure 3:
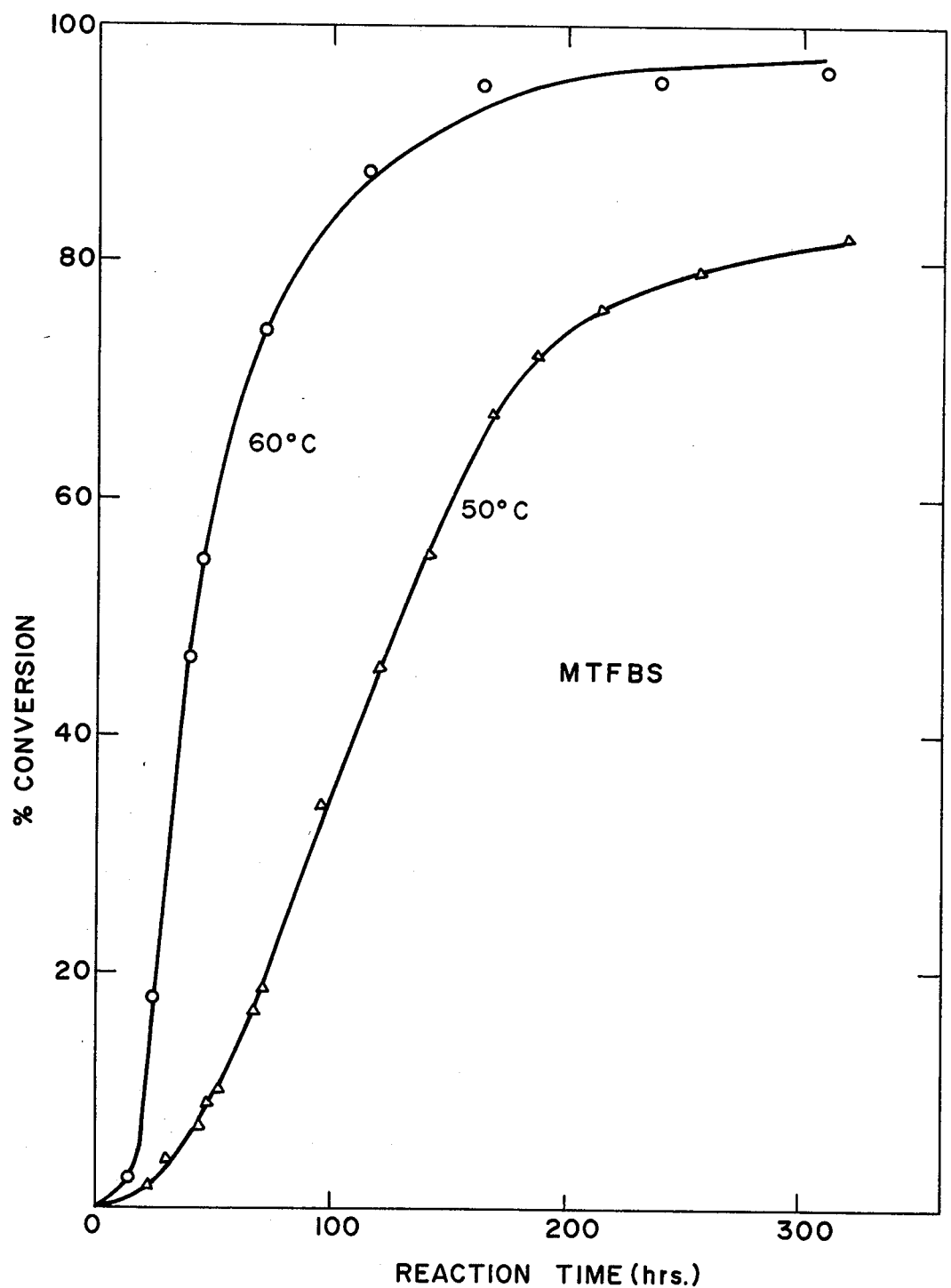
FIG. 3 illustrates the effect of thermal annealing of bis(m-trifluoromethylbenzenesulfonate) of 2,4-hexadiyn-1,6-diol (MTFBS) by a plot of percent conversion to polymer vs. reaction time in hours at a given temperature.

After polymerization has proceeded and is approaching the final value, the rate of polymerization decreases and the resulting top portion of the curve tends toward the abscissa, thus resulting in an "S"-shape. The length of the initial flat portion of the curve is a measure of the extent of the induction period and the steepness of the slope of the curve is a measure of the speed of the autocatalytic effect and thus the speed with which the contrasting color change occurs. As illustrated, the induction period for PFBS is 400 hrs. at 50° C., which represents about an eight-fold increase over that of PTS, measured under the same conditions. Similar polymerization characteristics are observed for MTFBS, the bis(m-trifluorobenzenesulfonate) of 2,4-hexadiyn-1,6-diol, upon thermal annealing as illustrated in FIG. 3. At 60° C., the induction period of PFBS is about 140 hrs., which represents about a seven-fold increase over that of PTS, measured under the same conditions.

Figure 2:
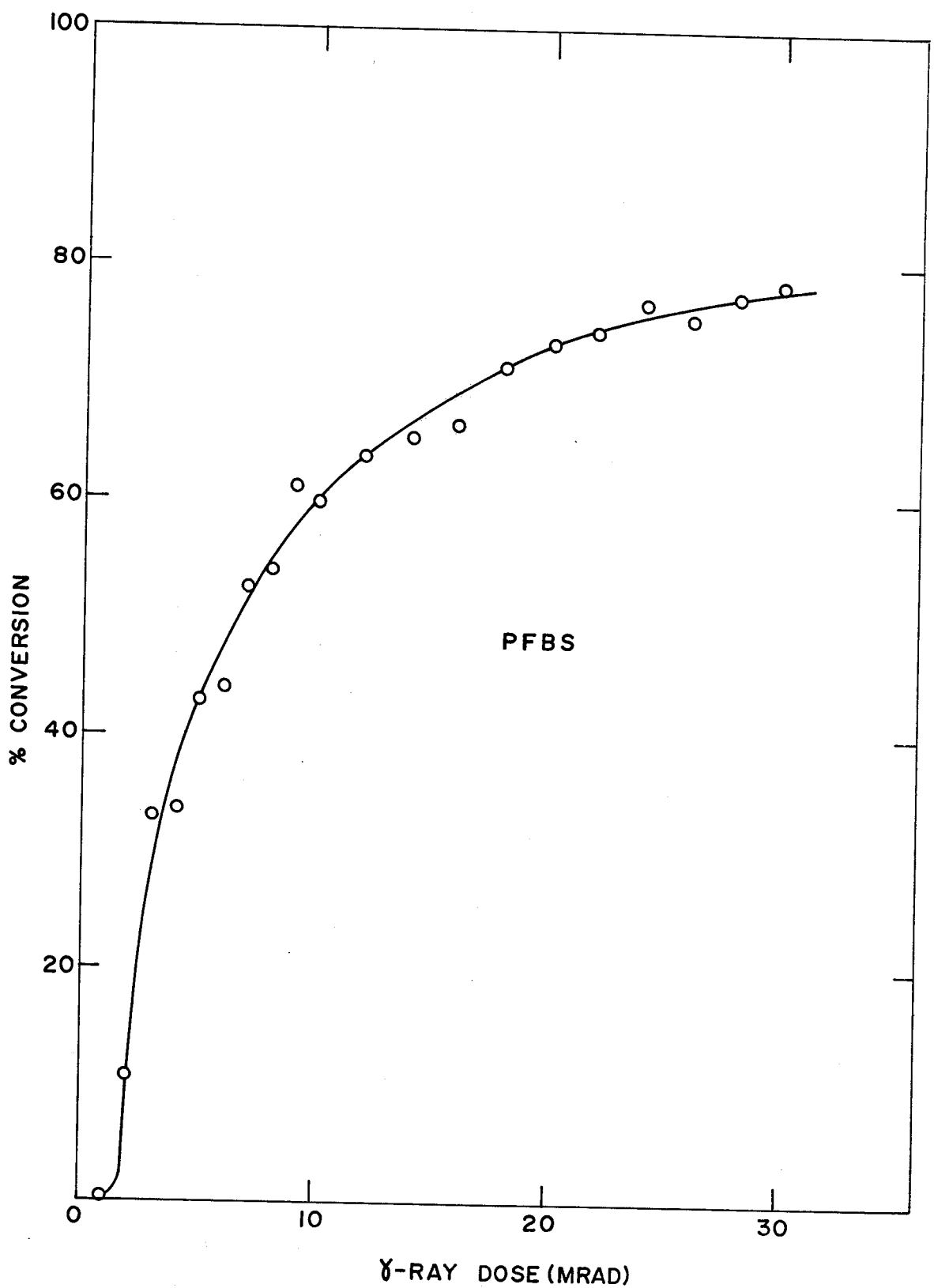
FIG. 2 illustrates the effect of gamma ray irradiation of bis(p-fluorobenzenesulfonate) of 2,4-hexadiyn-1,6-diol (PFBS) by a plot of percent conversion to polymer vs. gamma ray dosage in Mrads at ambient temperature.

The relatively long polymerization induction period of PFBS is most likely a direct consequence of its higher energy of activation, $E_{act}$, as compared to PTS. The energy of activation for PFBS is about 25.7 kcal/mole whereas that for PTS is about 21.9 kcal/mole, as determined from Arrhenius plots of the logarithms of the time in hours required to reach 50% polymerization versus the reciprocal of the reaction temperature in degrees Kelvin. Likewise, the energy of activation for MTFBS is calculated to be 24 kcal/mole by the above-described methods. The effect of gamma radiation on PFBS is illustrated in FIG. 2 wherein an autocatalytic effect is also observed. However, the effect is not as pronounced as is observed in FIG. 1 for thermal annealing.

Partially polymerized fluorinated benzenesulfonate diacetylene compositions are also a subject of this invention and comprise colored compositions containing up to 10 weight percent polymer derived from the subject monomeric compositions described herein. The partially polymerized compositions are actually colored solid solutions of polymer dissolved in a monomer matrix. The partially polymerized compositions can be prepared by thermal annealing, exposure to actinic radiation or high energy ionizing radiation for short periods of time thereby producing the composition. For example, partially polymerized PFBS composition can be prepared by thermal annealing at 60° C. for 140 hrs. or at 50° C. for 400 hrs., by exposure at room temperature to visible radiation for 30 days, to ultraviolet radiation (310 nm) for 150 hrs. or to high energy radiation, for example, gamma radiation, from a cobalt-60 source for a dosage from about 1 to 2 Mrads.

The resulting partially polymerized compositions are in general higher melting than the corresponding monomers. For example, partially polymerized PFBS has a melting point of 73°–80° C., as compared to 69° C. for the monomer.

The partially polymerized compositions are useful as reference standards, in a device incorporating the fluorinated benzenesulfonate diacetylene compositions of this invention as time-temperature history indicator materials, for assessing the extent of the color change occurring at the auto-catalytic step of the monitoring process. Such use will be obvious to one skilled in the art from a reading of this disclosure and that of U.S. Pat. No. 3,999,946, described hereinabove.

Polymer compositions are also a subject of the instant invention and comprise colored compositions containing from 10 to 100 weight percent of polymer derived from the subject monomeric compositions described herein. The polymer compositions are produced by similar methods described above for the partially polymerized compounds except that longer times, higher temperatures and larger radiation dosages are used. For example, fully polymerized PFBS is prepared by thermal annealing of the monomer at 60° C. for 150 to 250 hrs., exposure to visible radiation at 25° C. for 2 to 12 months, or exposure to gamma radiation for a dosage of 2 to 50 Mrads. The as-polymerized compositions can be extracted with a suitable solvent for the monomer, if desired, to yield a monomer-free composition. Suitable solvents include acetone, tetrahydrofuran, methanol and chloroform. The polymer compositions of this invention are useful as semiconductors, photoconductors and optical materials, and variations in methods of preparing these compositions and use thereof will be obvious to one skilled in the art from this disclosure.

Also a subject of this invention is an improved device for monitoring the time-temperature history of a perishable article including a housing, in which is positioned a time-temperature indicating material, capable of undergoing solid state polymerization upon thermal annealing to produce a contrasting color change, prior to the expiration of the shelf life of said article and means for observing said color change. The improvement in the device comprises providing a fluorinated benzenesulfonate diacetylene composition of this invention, as described herein, as the time-temperature history indicating material.

The basic elements of the device, the housing, a time-temperature indicating material capable of undergoing a color change upon thermal annealing, and means for observing the color change are well known in the art and are described in U.S. Pat. No. 3,999,946, hereby incorporated by reference, and for the sake of brevity will not be reiterated here. The improvement of the present invention device is directed to the nature of the time-temperature history indicating material, being the novel subject compositions described herein. Techniques for making and using the device, utilizing the compositions of this invention, disclosed herein, will be obvious to one skilled in the art from the teachings of both the present disclosure and the above-incorporated reference.

A preferred embodiment of the improved device comprises a fluorinated benzenesulfonate diacetylene composition of this invention, preferably one having a longer polymerization induction period, prior to undergoing a contrasting color change upon thermal annealing, as compared to the bis(p-toluenebenzenesulfonate) of 2,4-hexadiyn-1,6-diol, as measured under the same conditions; and preferably, said composition being the bis(p-fluorobenzenesulfonate) of 2,4-hexadiyn-1,6-diol.

The following examples are illustrative of the best mode of carrying out the invention as contemplated by us and should not be construed as being limitations on the scope or spirit of the instant invention.

EXAMPLE 1

Synthesis of 2,4-hexadiyn-1,6-diol bis(p-fluorobenzenesulfonate), (PFBS)

Into a 500 ml round bottom flask fitted with a mechanical stirrer, thermometer and addition funnel, was charged 11 grams (0.1 mole) 2,4-hexadiyn-1,6-diol, 100 ml of tetrahydrofuran and 47 grams (0.24 mole) of p-fluorobenzenesulfonyl chloride. The resulting mixture was stirred and cooled with an ice water bath. A solution of 20 grams potassium hydroxide, in 160 ml water, was added dropwise over a period of about 45 minutes at 7° to 10° C. After the addition was completed, the contents were stirred at 5° to 20° C. for an additional 5 hrs. At this point, the mixture was a dark brown color. The resulting mixture was poured into 500 ml of cold water and the resulting mixture was stirred for 2 hrs. The resulting brown precipitate was collected by filtration and washed with water to yield 29 grams (68% of theory) of product. The solid product was extracted with 500 ml. of diethyl ether and the ether extract evaporated to leave 26 grams (61% of theory) of pink crystals, melting point 70°–71° C. Analysis, for $C_{18}H_{12}O_6F_2S_2$, molecular weight, 426.404;

|  | C | H |
|---|---|---|
| Calculated: | 50.70 | 2.84 |
| Found: | 50.41 | 2.88 |

The infrared spectrum (KBr pellet) exhibited absorption bands at 3120, 2940, 2180, 1600, 1380, 1300, 1250, 1185, 1160, 1100, 1000, 950, 840 and 820 cm$^{-1}$.

EXAMPLE 2

Synthesis of 2,4-hexadiyn-1,6-diol bis(m-trifluoromethylbenzenesulfonate), (MTFBS)

Following the general synthetic procedure described in Example 1, 30 grams (0.123 mole) of m-trifluoromethylbenzenesulfonyl chloride was reacted with 5.5 grams (0.05 mole) 2,4-hexadiyn-1,6-diol in 50 ml tetrahydrofuran during the dropwise addition of a solution of 10 grams (0.175 mole) potassium hydroxide in 100 ml water. The resulting product was isolated and washed as described in Example 1 and extracted with diethyl ether to yield after evaporation of ether, 25.4 grams (96% of theory) of purple-red solid, melting point 64°–70° C. Recrystallization from 10% (v/v) acetone/petroleum ether yielded deep-red needles, melting point, 76°–78° C. Analysis for $C_{20}H_{12}O_6F_6S_2$:

|  | C | H |
|---|---|---|
| Calculated | 45.63 | 2.30 |
| Found | 45.67 | 2.48 |

The infrared spectrum (KBr pellet) exhibited absorption bands at 2180, 1610, 1440, 1375, 1320, 1180, 1120, 1075, 1000, 950, 850, 800 and 750 cm$^{-1}$.

EXAMPLE 3

Synthesis of 5,7-dodecadiyn-1,12-diol bis(p-fluorobenzenesulfonate), (4-D-PFBS)

Following the general synthetic procedure described in Example 1, 39.0 grams (0.20 mole) p-fluorobenzenesulfonyl chloride was reacted with 15.5 grams (0.08 mole) of 5,7-dodecadiyn-1,12-diol and 200 ml of diethyl ether at −5° to −9° C. except that finely powdered potassium hydroxide (56 grams, 1.0 mole) was added in portions, over a period of 30 minutes, instead of being added as an aqueous solution as in Example 1. This was done in order to increase the rate of reaction. After stirring at 3° to 16° C. for an additional 5 hours, the contents were poured into 500 ml. ice water, stirred to precipitate the product which was collected, washed and dried in air to yield 37 grams (90% of theory) of a light purple solid. The solid was washed with 500 ml.

diethyl ether to yield 21 grams (51% of theory) of a light pink powder, melting point 59°–62° C. Recrystallization from 10% (v/v) acetone/petroleum ether solvent yielded purple-colored crystals, melting point 69°–70° C. Analysis for $C_{24}H_{24}O_6F_2S_2$:

|  | C | H |
|---|---|---|
| Calculated | 56.46 | 4.74 |
| Found | 56.48 | 4.72 |

The infrared spectrum (KBr pellet) exhibited absorption bands at 2180, 1590, 1500, 1360, 1240, 1160, 1180, 1100, 960, 930 and 840 cm$^{-1}$.

EXAMPLE 4

Synthesis of 5,7-dodecadiyn-1,12-diol bis(m-triifluoromethylbenzenesulfonate), (4 D-MTFBS)

Following the general synthetic procedure of Example 1, 50 grams (0.202 mole) of m-trifluoromethylbenzenesulfonyl chloride was reacted with 15.5 grams (0.08 mole) of 5,7-dodecadiyn-1,12-diol, under nitrogen, and 200 ml of anhydrous ether, and 56 grams (1.0 mole) of finely powdered potassium hydroxide was added portion-wise over a period of 25 minutes at −7° to −5° C. After stirring at 0° C. to 15° C. for an additional 2.5 hours, the contents were poured into 500 ml. ice water, stirred to precipitate product, which was collected, washed and dried to yield 30 grams (61% of theory) of crude product. The product was dissolved in 400 ml diethyl ether, dried (over MgSO$_4$) and concentrated to a volume of 100 ml. mixture. At that stage, the solid in the mixture was collected by filtration yielding 15.7 grams (32% of theory) of a light red-purple solid, melting point 74°–77° C. Recrystallization from 10% (v/v) acetone/petroleum ether yielded purple-colored crystals, melting point 77°–78° C. Analysis for $C_{26}H_{24}O_6F_6S_2$:

|  | C | H |
|---|---|---|
| Calculated: | 51.15 | 3.96 |
| Found: | 51.10 | 4.00 |

The infrared spectrum (KBr pellet) exhibited absorption bands at 1370, 1340, 1180, 1140, 970 and 940 cm$^{-1}$.

EXAMPLE 5

Synthesis of 4,6-decadiyn-1,10-diol bis(m-trifluoromethylbenzenesulfonate), (3D-MTFBS)

Following the general synthetic procedure described in Example 1, 25 grams (0.1 mole) of m-trifluoromethylbenzenesulfonyl chloride was reacted with 6.5 grams (0.04 mole) of 4,6-decadiyn-1,10-diol in 120 ml of anhydrous ether, during the 15 minute portion-wise addition of 28 grams (0.5 mole) of powdered potassium hydroxide. The contents were stirred at 0° to 5° C. for 3 hrs. and poured into 300 ml of ice water. A white precipitate formed, which was collected by filtration and washed with cold water. The white solid was dissolved in ether, the resulting ether solution was dried and concentrated whereby crystallization occurred yielding 7.7 g (33% of theory) of a white solid, melting point, 67°–70° C. Recrystallization from cyclohexane yielded blue-colored crystals, melting point, 68°–69.5° C. Analysis for $C_{24}H_{20}O_6F_6S_2$:

|  | C | H |
|---|---|---|
| Calculated: | 49.49 | 3.46 |
| Found: | 49.90 | 3.58 |

The infrared spectrum (KBr pellet) exhibiited absorption bands at 1620, 1440, 1370, 1330, 1180, 1130, 1075, 1010, 970, 920, 840 and 810 cm$^{-1}$.

EXAMPLE 6

Thermal Polymerization Kinetics of 2,4-Hexadiyn-1,6-diol bis(p-fluorobenzenesulfonate) (PFBS) in the Solid State Tenth gram samples of powdered PFBS monomer (recrystallized from acetone/petroleum ether), sealed in glass tubes, were heated at three different temperatures for varying periods of time, resulting in the formation of the desired polydiacetylene, poly[2,4-hexadiyn-1,6-diol bis(parafluorobenzenesulfonate)]; poly (PFBS). Each heated sample was extracted with 50 ml of acetone at room temperature to remove any unreacted monomer, and the weight percent of monomer converted to polymer at that temperature and reaction time was determined, as illustrated in the following Tables A, B and C. The conversion vs. time curves (FIG. 1) for the thermal polymerization of PFBS are "S" shaped, i.e., the reaction rate proceeds slowly at the early stage of the reaction followed by a dramatic increase in reaction rate. Calculations (from these kinetic data at 50°, 60° and 66° C.) showed that the activation energy, $E_{act}$, for the thermal polymerization of PFBS is 26 kcal/mol. Usually, diacetylenes have $E_{act}$ values of 20–22 kcal/mole.

TABLE A

Weight Percent Monomer Converted to Polymer at 50° C.

| Time (hrs) | 0 | 272 | 335 | 408 | 433 | 463 | 487 | 512 | 519 |
|---|---|---|---|---|---|---|---|---|---|
| Wt. % | 0 | 1.4 | 2.4 | 9.6 | 13.8 | 20.2 | 27.0 | 33.6 | 38.7 |
| Time (hrs) | 543 | 552 | 575 | 614 | 648 | 840 | | | |
| Wt. % | 52.0 | 57.9 | 81.0 | 97.0 | 98.0 | 100 | | | |

TABLE B

Weight Percent of PFBS Monomer Converted to Polymer at 60° C.

| Time (hrs) | 0 | 45 | 72 | 96 | 110 | 118 | 129 | 137 | 148 |
|---|---|---|---|---|---|---|---|---|---|
| Wt % | 0 | 0 | 0 | 1.3 | 3.7 | 4.5 | 6.1 | 10.3 | 14.0 |
| Time (hrs) | 161 | 171 | 177 | 185 | 189 | 191 | 208 | 239 | 264 |
| Wt % | 25.2 | 40.0 | 50.0 | 66.4 | 76.5 | 83.0 | 95.5 | 97.0 | 97.2 |

TABLE C

Weight Percent of PFBS Monomer Converted to Polymer at 66° C.

| Time (hrs) | 0 | 48 | 60 | 70 | 75 | 77 | 78 | 84 | 93 |
|---|---|---|---|---|---|---|---|---|---|
| Wt % | 0 | 2.6 | 2.6 | 3.8 | 14.3 | 21.8 | 35.2 | 73.5 | 81.0 |
| Time (hrs) | 120 | 143 | | | | | | | |
| Wt % | 86.5 | 88.3 | | | | | | | |

EXAMPLE 7

Gamma-Ray Polymerization of PFBS in the Solid State

In separate runs, 0.2 g samples of PFBS monomer (mp. 68° C., crystallized from diethyl ether) were exposed to selected total dosages of Co$^{60}$ gamma-radiation at a dosage rate of 1 Mrad/hr, resulting in the formation of the desired poly(PFBS). Each irradiated sample was extracted with 50 ml of acetone at room temperature to remove any unreacted monomer, yielding the weight percent monomer converted to polymer indicated in Table D below. The conversion vs. dosage curve illustrated in FIG. 2, constructed from the values listed below, is also "S" shaped, although the autocatalytic effect is not as dramatic as in the thermal polymerization case.

TABLE D

Weight Percent of Irradiated PFBS Monomer Converted to Polymer

| Dose (Mrad) | 0 | 1 | 2 | 3 | 4 | 5 | 6 | 7 | 8 |
|---|---|---|---|---|---|---|---|---|---|
| Wt % | 0 | 0 | 10.7 | 33.4 | 33.9 | 43.0 | 44.0 | 53.4 | 53.8 |
| Dose (Mrad) | 9 | 10 | 12 | 14 | 16 | 18 | 20 | 22 | 24 |
| Wt % | 61.5 | 59.6 | 61.8 | 63.6 | 66.4 | 71.7 | 73.5 | 74.5 | 77.0 |
| Dose (Mrad) | 26 | 28 | 30 | | | | | | |
| Wt % | 76.0 | 77.5 | 79 | | | | | | |

EXAMPLE 8

Thermal Polymerization Kinetics of 2,4-Hexadiyn-1,6-diol bis(meta-trifluoromethylbenzenesulfonate) [MTFBS] in the solid state Following the general procedure of Example 6, 0.1 g samples of powdered MTFBS monomer (recrystallized from CCl$_4$), sealed in glass tubes, were heated in a temperature bath for certain periods of time, resulting in the formation of the desired polydiacetylene (poly MTFBS). Each heated sample was extracted with 50 ml of hot carbon tetrachloride to remove any unreacted monomer, yielding the weight percent of monomer converted to polymer indicated in following Tables E and F. The conversion vs. time curve illustrated in FIG. 3, constructed from the values listed below, for thermal polymerization of MTFBS is also "S" shaped. Calculations show that the $E_{act}$ for the thermal polymerization of MTFBS is 24 kcal/mole.

TABLE E

Weight Percent of MTFBS Monomer Converted to Polymer at 50° C.

| Time (hrs) | 0 | 24 | 31 | 46 | 48 | 54 | 68 | 72 | 96 | 120 |
|---|---|---|---|---|---|---|---|---|---|---|
| Wt % | 2.8 | 2.5 | 5.0 | 7.5 | 9.3 | 10.1 | 17.0 | 18.7 | 34.2 | 46.0 |
| Time (hrs) | 143 | 169 | 188 | 216 | 258 | 332 | | | | |
| Wt % | 55.5 | 67.8 | 72.8 | 76.0 | 79.0 | 82.0 | | | | |

TABLE F

Weight Percent of MTFBS Monomer Converted to Polymer at 60° C.

| Time (hrs) | 0 | 8 | 14.5 | 24.5 | 40 | 46 | 72 | 116 | 164 |
|---|---|---|---|---|---|---|---|---|---|
| Wt % | — | 3.5 | 2.3 | 17.7 | 46.5 | 55.0 | 74.0 | 87.5 | 94.5 |
| Time (hrs) | 240 | 310 | | | | | | | |
| Wt % | 94.2 | 95.8 | | | | | | | |

EXAMPLE 9

Construction of Time-Temperature History Monitoring Device from bis(para-fluorobenzenesulfonate) of 2,4-Hexadiyn-1,6-diol (PFBS)

(A) Purification of PFBS. About 9.3 g of PFBS was mixed with 3,000 ml of 50% (v/v) diethylether/petroleum ether. The resulting mixture was stirred at room temperature for 3 hrs. The small amount of insoluble material was removed by filtration. The filtrate was passed through a column (3 cm. diameter×32 cm. length) packed with a slurry of 110 g of silica gel (60–200 mesh) in 150 ml of 50% diethylether/petroleum ether. Concentration of the solution gave 7.5 g (81% recovery) of purified compound, mp 68°–70° C.

(B) Construction of a Device. About 0.9 g of the purified PFBS were dissolved in 150 ml of 10% (v/v) acetone/petroleum ether. The resulting solution was sprayed on a filter paper (22×28.5 cm) from a distance of about 15 cm. After drying the paper in air for about 5 mins., the coated filter paper appeared light pink. The coated paper was then cut into 2.5×2.5 cm squares, which were then used to monitor the time-temperature history profiles of perishable articles.

For example, one of the above-coated squares of filter paper exhibited a striking color change from dark red to gold at 60° C. At the beginning of the measurement, the PFBS was light pink in color. Upon further annealing at 60° C., the color intensified to a dark red after 6 days. However, after being annealed at 60° C. for 7 days, the indicator underwent a color change to a metallic gold.

The subject compositions of this invention are useful as time-temperature history indicating materials in devices for monitoring the time-temperature histories of perishable articles.

I claim:

1. A composition of the following formula:

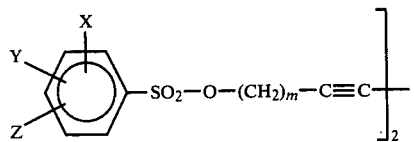

wherein m is an integer value from 1 to 4 and X, Y and Z are selected from hydrogen, fluoro and $C_1$–$C_4$ fluorinated normal, iso- or secondary alkyl, containing 1–9 fluorine atoms, said composition being symmetrical and containing at least two fluorine atoms and being capable of undergoing solid state polymerization upon thermal annealing or exposure to actinic radiation or high energy ionizing radiation.

2. The composition of claim 1 wherein X and Y are hydrogen.

3. The composition of claim 2 wherein Z is selected from m-fluoro, p-fluoro, m-trifluoromethyl and p-trifluoromethyl.

4. The composition of claim 3 selected from the group consisting of 2,4-hexadiyn-1,6-diol bis(p-fluorobenzenesulfonate), 2,4-hexadiyn-1,6-diol bis(m-trifluoromethylbenzenesulfonate), 4,6-decadiyn-1,10-diol bis(m-trifluoromethylbenzenesulfonate), 5,7-dodecadiyn-1,12-diol bis(m-trifluorobenzenesulfonate) and 5,7-dodecadiyn-1,12-diol bis(p-fluorobenzenesulfonate).

5. The composition of claim 4 being 2,4-hexadiyn-1,6-diol bis(p-fluorobenzenesulfonate).

6. A colored composition containing up to 10% by weight of a colored polymer of at least one monomer as defined in claim 1.

7. A colored composition containing from 10% to 100% by weight of a colored polymer of at least one monomer as defined in claim 1.

8. In a device for monitoring the time-temperature history of a perishable article including a housing, in which is positioned a time-temperature indicating material, capable of undergoing solid state polymerization upon thermal annealing to produce a contrasting color change, prior to the expiration of the shelf-life of said article, and means for observing said color change; the improvement which comprises providing a composition of claim 1 as the time-temperature history indicating material.

9. The device of claim 8 wherein said composition exhibits a longer induction period, prior to undergoing a contrasting color change upon thermal annealing, as contrasted to the bis(p-toluenesulfonate) of 2,4-hexadiyn-1,6-diol, as measured under the same conditions.

10. Device of claim 8 wherein the time-temperature indicating material is 2,4-hexadiyn-1,6-diol bis(para-fluorobenzenesulfonate).

11. Device of claim 8 wherein the time-temperature indicating material is 2,4-hexadiyn-1,6-diol bis(meta-trifluoromethylbenzenesulfonate).

12. In a device for monitoring the exposure history of a perishable article, during successive time intervals of exposure to the effects of temperature and/or radiation, said device comprising a housing in which is positioned an exposure indicating material capable, upon exposure to thermal annealing and/or to radiation, of undergoing a color change, and positioned to allow observation of said color change; the improvement which consists essentially in providing a composition of claim 1 as the exposure indicating material.

* * * * *